United States Patent
Najafi et al.

(10) Patent No.: US 6,426,066 B1
(45) Date of Patent: Jul. 30, 2002

(54) USE OF PHYSIOLOGICALLY BALANCED, IONIZED, ACIDIC SOLUTION IN WOUND HEALING

(75) Inventors: Ramin Najafi, Novato; Suzanne M. Bernard, San Francisco, both of CA (US)

(73) Assignee: California Pacific Labs, Inc., Novato, CA (US)

( * ) Notice: Subject to any disclaimer, the term of this patent is extended or adjusted under 35 U.S.C. 154(b) by 0 days.

(21) Appl. No.: 09/482,159

(22) Filed: Jan. 12, 2000

(51) Int. Cl.$^7$ .................. A61K 31/74; A61K 33/40; A61K 33/14

(52) U.S. Cl. ................. 424/78.04; 424/78.06; 424/78.07; 424/613; 424/661

(58) Field of Search ............ 424/78.04, 78.06, 424/78.07, 613, 661; 205/701, 742; 204/228, 229

(56) References Cited

U.S. PATENT DOCUMENTS

| | | | |
|---|---|---|---|
| 5,622,848 A | 4/1997 | Morrow | 435/173.1 |
| 5,731,008 A * | 3/1998 | Morrow | 424/613 |

FOREIGN PATENT DOCUMENTS

| | | | |
|---|---|---|---|
| WO | WO 99/34652 | 7/1999 | H05F/3/00 |

OTHER PUBLICATIONS

"Aids Treatment w/ Nonlethal Intravenous Ozone solution", Mark E. Bruk, Bionet.Virology,1995.*

"Spectroscopic Characterization and the pH Dependence of Bactericidal Activity of the Aqueous Chlorine Solution", Nakagawar et al., Anayltical Sciences, vol. 14 No. 4, 691–698.*

H. Hayashi et al., "Successful Treatment of Mediastintis after Cardiovascular Surgery Using Electrolyzed Strong Acid Aqueous Solution",*Artificial Organs*, 21(1), pp. 39–42 (1997).

N. Horiba et al., "Bactericidal effect of electrolyzed neutral water on bacterial isolated from infected root canals", *Oral Surg Oral Med Oral Pathol Oral Radiol Endod* 1999, Jan; 87(1):83–7.

Y. Inoue et al., "Trial of Electrolyzed Strong Acid Aqueous Solution Lavage in the Treatment of Peritonitis and Intraperitoneal Abscess", *Artficial Organs*, 21(1), pp. 28–31 (1997).

A. Iwasawa and Y. Nakamura, "Bactericidal effect of acidic electrolyzed water—comparison of chemical acidic sodium hydrochloride (NaOCl) solution", *J. Jap. Assoc. Infec. Diseases*, 70(9), pp. 915–922 (1996).

X. W. Li et al., "Preliminary study of microbiocide effect and its mechanism of electrolyzed oxidizing water", *Chinese J. Epidem.*, 17(2), pp. 95–98 (1996).

M. Miyamoto et al., "Effectiveness of acidic oxidative potential water in preventing bacterial infection in islet transplantation", *Cell Transplant* 1999 Jul.–Aug;8(4):405–11.

S. Sekiya et al. "Treatment of Infectious Skin Defects or Ulcers with Electrolyzed Strong Acid Aqueous Solution", *Artificial Organs*, 21(1), pp. 32–38(1997).

J.B. Selkon et al., "Evaluation of the antimicrobial activity of a new super–oxidized water, Sterilox®, for the disinfection of endoscopes", *J. Hosp. Infec.*, 41(1), pp. 59–70 (Jan. 1999).

H. Tanaka et al., "Antimicrobial activity of superoxidized water", *J. Hosp. Infect.*, 34(1), pp. 43–49 (1996).

N. Tanaka et al. "The Cleaning and Disinfecting of Hemodialysis Equipment Using Electrolyzed Strong Acid Aqueous Solution", *Artificial Organs*, 23(4), pp. 303–309 (Apr. 1999).

K.S. Venkitanarayanan et al., "Efficacy of Electrolyzed Oxidizing Water for Inactivating *Escherichia coli* O157:H7, *Salmonella enteritidis*, and *Listeria monocytogenes* ", *Appl. & Env. Microbiol.*, 65(9), pp. 4276–4279 (Sep. 1999).

* cited by examiner

Primary Examiner—Zohreh Fay
Assistant Examiner—Brian-Yong S. Kwon
(74) Attorney, Agent, or Firm—Kenyon & Kenyon

(57) ABSTRACT

A physiologically-balanced, ionized, acidic solution. The solution may be prepared by the electrolysis of a solution comprising a mixture of inorganic salts in physiologically balanced proportions. A mixture of inorganic salts and, optionally, minerals (such as metallic elements, for example, and not by way of limitation) is used in order to mimic the electrolyte concentration and mixture of body fluid in an isotonic state. The solution typically comprises halide salts of sodium, potassium, calcium, and other cations. Typically the halide is fluoride, chloride, bromide, or iodide; and most typically chloride. The halide-comprising acidic solution is physiologically balanced by the inclusion of elements such as sodium, potassium, magnesium, zinc, lithium, and beryllium in the solution. The composition of the invention is nontoxic and has antibacterial properties. The composition is useful in any application in which antimicrobial properties are desirable, particularly in the topical application to wounds, burns, etc., and can be incorporated into a bandage or wound dressing.

15 Claims, 3 Drawing Sheets

USE OF PHYSIOLOGICALLY BALANCED, IONIZED, ACIDIC SOLUTION IN WOUND HEALING

BACKGROUND OF THE INVENTION

1. Field of the Invention

This invention relates to a physiologically balanced, ionized, acidic solution that is useful in wound healing and other applications in which antimicrobial properties are desirable. Preferably, the ionized solution is prepared by electrolysis, i.e. it is an electrolyzed solution. In addition, the invention relates to a methodology of using the solution of the invention, including a specialized bandage which may be used in combination with the solution or with other solutions or topically applied materials.

2. Brief Description of the Background Art

Various electrolyzed acidic salt solutions, their properties, and their uses have been described in the art. Several examples are provided below.

U.S. Pat. No. 5,622,848, issued Apr. 22, 1997, to Morrow, discloses a microbicidal solution for in vivo and in vitro treatment of microbial infections. The solution comprises an electrolyzed saline containing regulated amounts of ozone and active chlorine species, wherein the ozone content is between about 5 and 100 mg/L, and the active chlorine species content is between about 5 and 300 ppm. The active chlorine species comprises free chlorine, hypochlorous acid, and the hypochlorite ion, as measured by a chlorine selective electrode. The solution is prepared by subjecting a 1% or less saline solution to electrolysis under conditions sufficient to produce the desired active ingredients. The solution is preferably utilized at an isotonic saline concentration, and may be adjusted with hypertonic saline. The solution may be used for in vitro treatment of infected whole blood, blood cells, or plasma to reduce contamination, and may be used in the treatment of fluids infected with HIV, hepatitis, and other viral, bacterial, and fungal agents. The solution may also be administered to warm-blooded animals, including humans, by intravenous injection or other modes, for similar purposes.

PCT publication No. WO9934652, published Jul. 8, 1999, of Marais, discloses the use of an electrochemically activated sodium hypochlorite-free irrigating medium to reduce the proliferation of bacteria and other microorganisms during tooth root canal. Anion-and cation-containing solutions are obtained by electrolysis of a 10% aqueous NaCl solution. The anion-containing solution is used at a pH of about 2–7 and an oxidation reduction potential (ORP) of about +1170 mV; the cation-containing solution is used at a pH of about 7–13 and an ORP of about −980 mV.

X. W. Li et al. (*Chinese J. Epidem.*, 17(2), pp. 95–98, 1996) reported a preliminary study of the microbicidal effect of electrolyzed oxidizing water. Electrolyzed oxidizing water was shown to completely kill *Staphylococcus aureus* and *Escherichia coli* within 15 seconds, while 10 minutes were required to completely kill all spores of *Bacillus subtilus var. niger*. Thirty seconds were needed to destroy the antigenicity of HBsAg. The oxidation reduction potential and pH values of electrolyzed oxidizing water were not significantly changed when stored for three weeks at room temperature under air-tight, light-free conditions.

A. Iwasawa et al. (*J. Jap. Assoc. Infec. Diseases*, 70(9), pp. 915–922, 1996) evaluated the bactericidal effect of acidic electrolyzed water on *S. aureus, S. epidermidis*, and *Pseudomonas aeruginosa*. At pH 5.0 to approximately 6.0, three bacterial strains were killed soon after being exposed to the acidic water containing 50 mg/L chloride, and the chloride concentration reportedly did not change after standing open for 6 hours. At pH 2.67 to approximately 2.80, the bactericidal effects were observed at a chloride concentration of 5 mg/L, and 80% of the chloride reportedly remained after standing open for 6 hours.

H. Tanaka et al. (*J. Hosp. Infect.*, 34(1), pp. 43–49, 1996) reported on the antimicrobial activity of superoxidized water. Superoxdized water is described as "a strong acidic and colorless solution with a high oxidation-reduction potential. The solution is prepared by mixing a small amount of salt with tap water in an electrolyser". The antimicrobial activity of superoxidized water was tested against methicillin-sensitive *S. aureus, Serratia marcescens, E. coli, P. aeruginosa*, and *Burkholderia cepacia*. The number of bacteria was reduced below the detection limit following incubation in superoxidized water for 10 seconds. The bactericidal activity of superoxidized water was similar to that of 80% ethanol, but superior to that of 0.1% chlorhexidine and 0.02% povidone iodine.

Y. Inoue et al. (*Artificial Organs*, 21(1), pp. 28–31, 1997) reported on the use of electrolyzed strong acid aqueous solution lavage in the treatment of peritonitis and intraperitoneal abscess. Peritoneal and abscess ravages were performed using an electrolyzed strong acid aqueous solution to treat seven patients with peritonitis and intraperitoneal abscesses. The period of irrigation in the seven patients ranged from 9 to 12 days, with conversion to microorganism negative state observed within 3 to 7 days. The authors describe the solution as being "acidic water that contains active oxygen and active chlorine and possesses a redox potential"

S. Sekiya et al. (*Artificial Organs*. 21(1), pp. 32–38, 1997) reported on the use of electrolyzed strong acid solutions in the treatment of infectious skin defects and ulcers using. The clinically applied therapy of electrolyzed strong acid aqueous solutions were found to be effective in the treatment of infectious ulcers. Sekiya et al. describe the strong aqueous solution (ESAAS) as being "generated by electrolyzing water and a small quantity of salt with a cation transfer filter."

H. Hayashi et al. (*Artificial Organs*, 21(1), pp. 39–42, 1997) reported on the use of electrolyzed strong acid aqueous solutions (ESAAS) in the treatment of mediastinitis following cardiovascular surgery. Hayashi et al. described ESAAS as being "produced by electrolyzing sodium chloride solution. ( . . . ) ESAAS is produced by electrolyzing the sodium chloride solution using an ion-exchange membrane that separates the positive and negative electrodes. A small amount of sodium chloride is added to the water to facilitate electrolysis and increase the concentration of dissolved chloride." The mediastinal wound was left open and irrigated with ESAAS one to three times daily until the infection was eradicated. Satisfactory growth of granulation tissue was observed in all patients treated, with no evidence of adverse effects attributable to ESAAS.

N. Tanaka et al. (*Artificial Organs*, 23(4), pp. 303–309, April 1999) reported on the use of electrolyzed strong acid aqueous solutions to clean and disinfect hemodialysis equipment. The solutions were found to directly inactivate bacterial endotoxins, and proved to be more economical than the conventional disinfecting method. The "electrolyzed strong acid aqueous solutions are disclosed to be "strongly acidic water which is made by electrolyzing tap water containing 50–1000 ppm salt (NaCl >99% pure) in a cell partitioned by a polyester diaphragm. It has an acidity of 2.3–2.7 pH, more than 1,000 mV in oxidation-reduction potential and 10–50 ppm in available: chlorine."

J. B. Selkon et al. (*J. Hosp. Infec.*, 41(1), pp. 59–70, January 1999) evaluated the antimicrobial activity of a new superoxidized water, STERILOX® (Sterilox Medical Limited, 85 E Milton Park, Abingdon, Oxon OX14 4RY, UK) for the disinfection of endoscopes. This superoxidized water is described as being "generated at the point of use by passing a saline-solution over coated titanium electrodes at 9 amps. The product generated has a pH of 5.0–6.5 and an oxidation reduction potential of >950 mV." The antimicrobial activity of STERILOX® was tested against *Mycobacterium tuberculosis, M. avium-intracellulare, M. chelonae, E. coli* (including type 0157), *Enterococcus faecalis, P. aeruginosa, B. subtilus var. niger* spores, methicillin-resistant *S. aureus, Candida albicans*, poliovirus type 2, and human immunodeficiency virus HIV-1. Under clean conditions, freshly generated STERILOX® was found to be highly active against all these microorganisms, giving a 5 log, (99.999%) or greater reduction in 2 minutes or less.

K. S. Venkitanarayanan et al. (*Appl. & Env. Microbiol.*, 65(9), pp. 4276–4279, September 1999) evaluated the efficacy of electrolyzed oxidizing water for inactivating *E. coli* O157:H7, *Salmonella enteritidis*, and *Listeria monocytogenes*. A five-strain mixture of *E. coli* O157:H7, *S. enteritidis*, or *L. monocytogenes* was inoculated in electrolyzed oxidizing water at various temperatures, for various time periods. The electrolyzed oxidizing water is produced from a saline base solution containing approximately 12% by weight NaCl. At 4° C. and 23° C., an exposure time of 5 minutes, the population of all three pathogens in the treatment samples was reported to be reduced by approximately 7 log CFU/mL, with compete inactivation by 10 minutes of exposure. A reduction of greater than 7 log CFU/mL in the levels of the three pathogens was reported to occur in the treatment samples incubated for 1 minute at 45° C. or for 2 minutes at 35° C.

SUMMARY OF THE INVENTION

This invention relates to physiologically balanced, ionized, acidic solutions and to 11 a methodology for their use, including a specialized bandage which may be used in combination with the solutions, or with other topically applied materials. Preferably the ionized solutions are prepared by electrolysis, i.e. they are electrolyzed solutions.

The composition of the invention is prepared using a mixture of inorganic salts in physiologically balanced proportions. A mixture of inorganic salts and, optionally minerals, (such as metallic elements, for example and not by way of limitation) is used in order to mimic the electrolyte concentration and mixture of body fluid in an isotonic state. The solution typically comprises halide salts of sodium, potassium, calcium, and other cations. Typically the halide is fluoride, chloride, bromide, or iodide, and most typically chloride. The concentrations of these salts in combination with particular minerals are such that they give the electrolyzed composition its unique properties.

In accordance with the present invention, we have created a composition comprising a physiologically balanced, electrolyzed acidic solution, where the starting solution prior to electrolysis comprises a total concentration of halide-comprising salts ranging from about 0.4 g/L to about 16 g/L; more preferably ranging from about 4 g/L to about 12 g/L; and, most preferably, ranging from about 5.2 g/L to about 6.2 g/L. The solution may optionally contain other salts or minerals. The electrolyzed solution has a pH within the range of about 2 to about 6, an oxidation reduction potential within the range of about +600 mV to about +1200 mV, and a titratable halide (X) content within the range of about 10 ppm to about 100 ppm, where X is $F^-$, $Cl^-$, $Br^-$, or $I^-$.

The starting solution used to prepare the physiologically balanced, electrolyzed, acidic composition of the invention preferably comprises a plurality of halide-comprising salts selected from the group consisting of sodium halide, potassium halide, magnesium halide, calcium halide, zinc halide.

The starting solution of halide-comprising salts, and optionally-other salts and minerals, is converted to acidic water through electrolysis. The electrolyzed, halide-comprising solution has a typical oxidation reduction potential (ORP) of about +600 to +1200 mV. The pH of the electrolyzed, chlorine-comprising solution is typically lowered to about 6 or less, giving the solution bactericidal, fungicidal, and sporicidal properties. The halide-comprising acidic solution is physiologically balanced by the inclusion of elements such as sodium, potassium, magnesium, zinc, lithium, and beryllium in the solution. Typically these elements are supplied in the form of halide-comprising salts which are ionized during electrolysis. Preferably, these physiologically-balancing halide-comprising salts are selected from the group consisting of sodium halide, potassium halide, magnesium halide, zinc halide, lithium halide, beryllium halide, and combinations thereof. Most preferably the salts are selected from sodium chloride, potassium chloride, magnesium chloride, zinc chloride, and combinations thereof.

A particularly preferred starting solution for preparation of the electrolyzed solution includes sodium chloride present at a concentration ranging from about 0.3 g/L to about 14 g/L, potassium chloride present at a concentration ranging from about 0.02 g/L to about 0.8 g/L, and magnesium chloride present at a concentration ranging from about 0.01 g/L to about 0.5 g/L, prior to electrolysis.

The electrolyzed acidic solutions contain, among other components, hydroxyl free radicals, oxygen, ozone, hypochlorous acid, hydrochloric acid, and hydrogen peroxide. These are the same oxidizing agents involved in physiological systems associated with wound healing and tissue repair and regeneration. For example, hypochlorous acid is the chief bactericidal agent produced by neutrophils at sites of inflammation, injury, and wounds. An adequate supply of oxygen is particularly important in collagen synthesis. In vitro studies have shown that the rate at which fibroblasts synthesize collagen is proportional to the extracellular oxygen concentration. In addition, increased crosslinking of collagen fibers, which is responsible for the increase in tensile strength of collagen, is observed in healing skin wounds with increases in the concentration of available oxygen. In vivo studies have also shown that granulation tissues in healing leg ulcers exposed to excess oxygen are characterized by abundant fibroblast proliferation.

The solutions of the invention are physiologically balanced and, when applied to infected wounds, enhance the process of healing substantially. Antimicrobial properties of acidic water solutions have been tested against many organisms, including *Escherichia coli, Listeria monocytogenes, Staphylococcus aureus*, methicillin-resistant *S. aureus* (MRSA), *Pseudomonas aeruginosa*, Lactobacillus, yeast, vancomycin-resistant enterococcus, molds, and spores. Vancomycin-resistant bacteria, MRSA, and others are easily destroyed by the solutions of the present invention. The solutions of the invention are osmotically balanced, environmentally friendly, and have minimal cytotoxicity. For example, no cytotoxicity was observed in rabbits' eyes nor in in vitro cytotoxicity studies carried out to date.

The composition of the invention is nontoxic and has antibacterial properties. The composition is useful in any application in which antimicrobial properties are desirable. Such applications include, without limitation, treatment of wounds, burns, and canker sores; irrigation; cleaning of tissue sites (e.g., pre- and post-operative); ophthalmic applications (e.g., in contact lens cleaning solutions or for irrigation of the eye during ophthalmic surgery); for dermatological applications, psoriasis; and numerous applications which are readily apparent to one skilled in the art. Unlike many other solutions used in similar applications, the composition of the invention has minimal to no side effects. For example, in Draize testing in Rabbit eyes, when compared to other antiseptic solutions, the physiologically balanced, electrolyzed, acidic solution of the present invention behaves in a manner similar to saline solution. he composition of the invention can be incorporated into a bandage or wound dressing, as described subsequently herein. The physiologically balanced, electrolyzed, acidic solution may be used in combination with a specially designed bandage in a wound treatment protocol as described subsequently herein. The specialized bandage includes an opening or "window" through which topical treatment materials such as the solution of the present invention may be applied.

Also disclosed herein is an article of manufacture comprising the composition of the invention packaged in a container. Surfaces of the container which are in contact with the composition of the invention are made of material which is not reactive with an oxidizing agent.

DETAILED DESCRIPTION OF THE INVENTION

Figure 1:
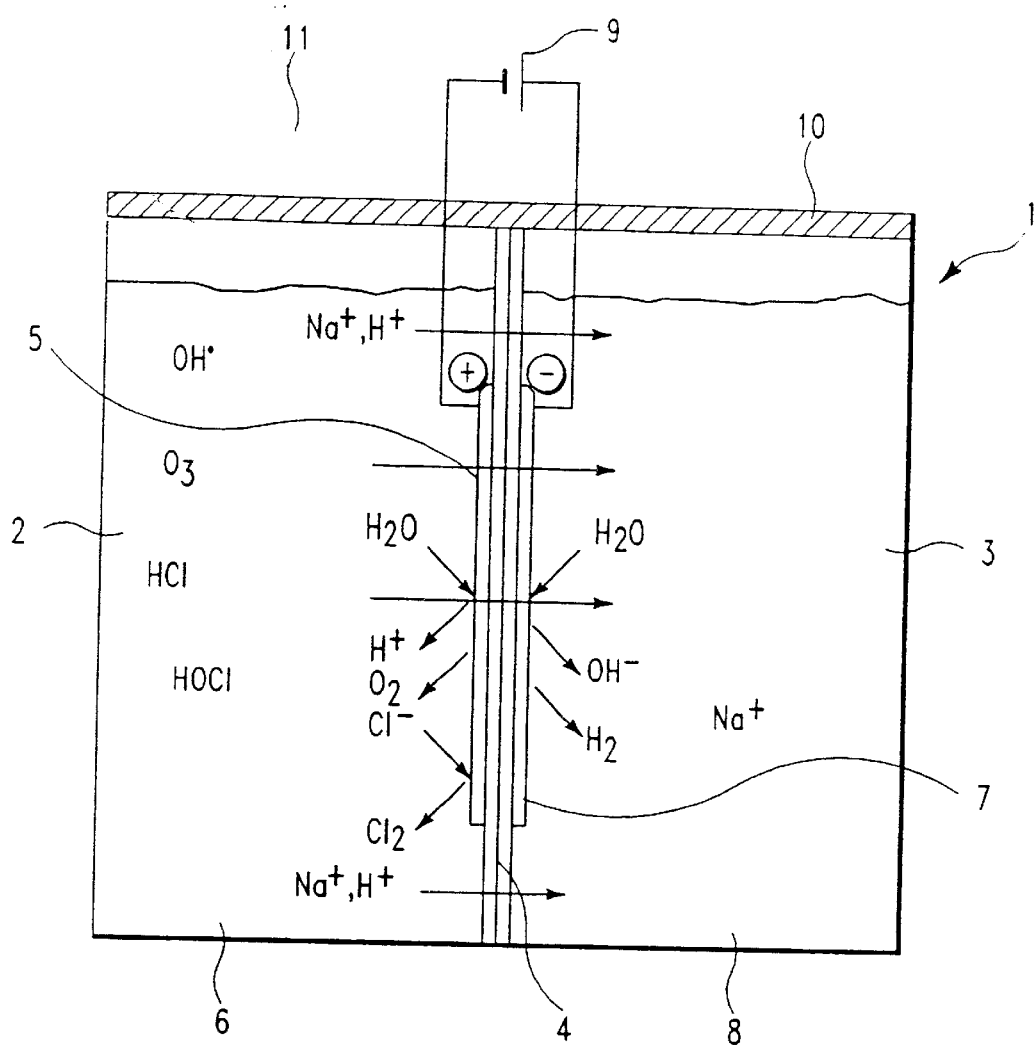
FIG. 1 is a cross-sectional schematic of an electrolyzing unit 1 having two compartments, identified in FIG. 1 as elements 2 and 3. Compartments 2 and 3 are separated by a semipermeable membrane 4. A positive electrode 5 is located in compartment 2, where a strong acidic solution 6 is generated. A negative electrode 7 is located in compartment 3, where an alkaline solution 8 is generated. Electrodes 5 and 7 are connected to a power source 9 which generates a current across semipermeable membrane 4. A lid 10 keeps electrolyzing unit 1 free from ambient air 11.

Described herein are a physiologically balanced, electrolyzed, acidic solution; methods and apparatus used in the production of the solution; methods for use of the solution, including the description of a specialized bandage for administering the solution or other topically applied treatment materials. Also disclosed are recommended packaging for the solution.

I. THE COMPOSITION OF THE INVENTION

The present invention is a physiologically balanced, electrolyzed acidic solution, which is generated from a starting solution comprising a total concentration of halide-comprising salts ranging from about 0.4 g/L to about 16 g/L; more preferably ranging from about 4 g/L to about 12 g/L; and most preferably ranging from about 5 g/L to about 6 g/L. Optionally, minerals may be added, depending on the end use application.

A typical starting solution, prior to electrolysis, by way of example and not by way of limitation, may comprise a plurality of chloride-comprising salts selected from the group consisting of sodium chloride, potassium chloride, magnesium chloride, calcium chloride, zinc chloride, and combinations thereof. Additional chloride-comprising salts such as lithium chloride and beryllium chloride may be added, depending on the application.

For purposes of providing particular physiologically balancing characteristics, combinations of various halogen-comprising salts may be used. For example, and not by way of limitation, sodium chloride may be used in combination with potassium fluoride, which may be used in combination with lithium iodide.

A mixture of salts, providing varying cations to the starting solution, enables mimicing of the electrolyte concentration and mixture of body fluid in an isotonic state. The various salts are provided in particular concentration ranges which give the composition its unique properties.

Preferred concentration ranges for the various chlorine-comprising salts to be used in the starting solution used to prepare an electrolyzed solution are presented in Table 1, below.

TABLE 1

Compositions of preferred Chloride-Containing Salts In Preferred Embodiment Starting Solutions For Preparation Of An Electrolyzed Acidic Solution

|  | Preferred | More Preferred | Most Preferred |
| --- | --- | --- | --- |
| NaCl (g/L) | 0.33–14.6 | 3.6–11.0 | 4.7–5.5 |
| KCl (g/L) | 0.02–0.9 | 0.2–0.7 | 0.3–0.33 |
| MgCl$_2$ (g/L) | 0.01–0.5 | 0.1–0.4 | 0.16–0.19 |

The properties of the physiologically balanced, electrolyzed acidic solutions produced from the Starting Solutions described in Table 1 are presented in Table 2, below.

TABLE 2

Properties of Preferred Physiologically-Balanced Electrolyzed Acidic Solutions Generated From The Starting Solutions Listed in Table 1

|  | Preferred | More Preferred | Most Preferred |
|---|---|---|---|
| ORP (mV) | +600 to +1200 | +800 to +1160 | +1000 to +1150 |
| pH | 2.0–6.0 | 2.2–4.5 | 2.4–3.5 |
| HClO Conc. (ppm) | 0.1–1000 | 1–500 | 10–100 |
| $O_3$ conc. (ppm) | 0.001–5 | 0.01–3 | 0.1–1.5 |
| Soluble $O_2$ Conc. (ppm) | 5–30 | 10–25 | 20–25 |

As shown in Table 3, below, the physiologically-balanced, electrolyzed acidic solution of the invention and tap water typically have very different properties.

TABLE 3

Comparison Of Properties of A Preferred Physiologically-Balanced Electrolyzed Acidic Solution and Typical Tap Water

|  | Electrolyzed Acidic Saline Solution (Typical Properties) | Tap Water |
|---|---|---|
| Opr (mV) | +1146 | +740 |
| pH (at 18° C.) | 2.5 | 7.3 |
| Conductivity (s/cm) | 1980 | 245 |
| HClO (ppm) | 10 | 0.4 |
| $Ca^{++}$ (ppm) | 21 | 26 |
| $Mg^{++}$ (ppm) | 36 | 6.7 |
| $Na^+$ (ppm) | 1,600 | 16 |
| $K^+$ (ppm) | 190 | 2.4 |
| $Cl^-$ (ppm) | * | 27 |
| Soluble $O_2$ (ppm) | 25 | * |

*Not measured.

II. APPARATUS AND METHOD FOR MAKING THE PHYSIOLOGICALLY BALANCED, ELECTROLYZED ACIDIC WOUND HEALING SOLUTIONS

The physiologically-balanced, acidic solution of the invention is prepared using electrolysis. Electrolysis of water is the process by which the hydrogen ions are reduced, providing hydrogen gas, and the hydroxide ions are oxidized, providing oxygen gas.

The wound healing solution described herein was prepared using a SUNTRON® MWB-2 model electrolyzing unit of the kind manufactured by Koshin Co. Ltd., Kyoto, Japan. Equivalent wound healing solutions can be prepared using a SUPER OXSEED LABO® electrolyzing unit of the kind manufactured by ARV Co., Japan.

With reference to FIG. 1, which shows a general schematic of an electrolyzing unit in which a physiologically balanced, electrolyzed, acidic wound healing solution is prepared, and with reference to the SUNTRON® MWB-2 model electrolyzer, the electrolyzing unit 1 has a first compartment 2 and a second compartment 3, each of which have a capacity of about 3 liters. Compartments 2 and 3 are separated by a semi-permeable membrane 4. In the first compartment 2, a positive electrode 5 is located. In the first compartment 2 a strong acidic solution 6 is generated. In the second compartment 3, a negative electrode 7 is located In the compartment 3, an alkaline solution 8 is generated. Electrodes 5 and 7 are connected to a power source 9 which generates a 0.9 A, 100V current. A lid 10 keeps the electrolysis unit free from contamination by ambient air 11.

A salt mixture was prepared by adding 14.2 g of KCl (J. T. Baker), 8.05 g of $MgCl_2$, $6H_2O$ (J. T. Baker) and 235.5 g of NaCl (non-iodated, Morton). This salt mixture was added to tap water at a concentration of 5.38 g per Liter of water to prepare a starting solution. 2.5 L of solution was placed in first Compartment 2 and 2.5 L of solution was placed in second Compartment 3. The power source 9, shown in FIG. 1, was turned on and power was applied for 15 minutes. The electrolysis was carried out at room temperature (about 25° to 30° C.), with no external heat added and no heat removed.

Salt solutions allow currents to pass between the electrodes, accelerating the process of electrolysis. The amount of salt necessary to affect the electrolysis process is minimal. During the electrolysis process, a halide salt, such as sodium chloride is in ionized form, as shown below.

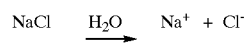

During electrolysis of saline, the sodium ions are attracted to the negatively charged electrodes, and will counterbalance the hydroxide ions on the alkaline side; the chloride ions travel to the positive electrode. The chloride ions then undergo an oxidative process which results in the generation of small quantities of chlorine gas that are immediately consumed to form hypochlorous acid, as illustrated below.

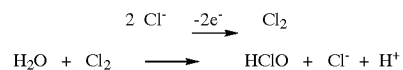

Chloride ions in saline are in the form of either HClO, $ClO^-$, or $Cl^-$; the balance among these ions is greatly affected by the pH of the solution. Only HClO and $ClO^-$ ions are effective sterilizing agents, with HClO being ten times more effective than $ClO^-$. In acidic pH, most of the $ClO^-$ ions are in the form of HClO. Under electric current, low levels of $O_3$ are formed according to the following reactions.

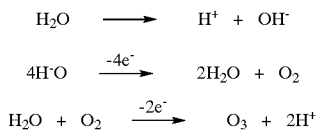

The combination of hypochlorous acid and ozone synergistically enhances the anti-microbial properties of the solution of this invention.

Other halide salts undergoing electrolysis participate in similar ionization processes, which are well known and documented in the art.

The properties of the physiologically-balanced, electrolyzed acidic solution prepared in the manner described above are presented in Table 3.

A typical physiologically-balanced, electrolyzed acidic solution of the invention has a concentration of sodium cations ranging from about 0.005 g/L to about 7 g/L, a concentration of potassium cations ranging from about 0.005 g/L to about 0.6 g/L, a concentration of magnesium cations ranging from about 0.005 g/L to about 0.1 g/L. It is the presence of this combination of cations, and optionally other cations previously described, which provide the physiological balancing of the electrolyzed acidic solution.

A typical physiologically-balanced, electrolyzed acidic solution produced using the starting materials described of the invention has a low pH (about 2 to about 6), an HClO concentration of about 0.1 ppm to about 1000 ppm, an $O_3$ concentration of about 0.001 ppm to about 5 ppm, and an $O_2$ concentration of about 5 ppm to about 30 ppm. This combination of chemicals gives the electrolyzed acidic saline solution of the invention its superior antiseptic ability.

Standard electrolysis equipment, including the particular apparatus named herein, can be used in the manufacture of the electrolyzed salt solutions of the invention, as previously mentioned.

Following manufacture, the solutions of the invention must be stored for use. Packaging is very important in extending the useful shelf life of the solutions. In particular, the surfaces of the container which make contact with the solution should be made of a material which tends not to react with oxidizing agents.

We evaluated a number of different container materials, and surprisingly discovered that while a glass contacting surface preserves the long term strength (potency) of the solution, plastic surfaces are, in general, not as helpful. By way of example and not by way of limitation, chemically resistant, coated soda lime amber glass 1 L or 500 mL bottles (manufactured by Lawson Mardon Wheaton, Millville, N.J. 08332), meeting the requirements for Type III as established by the United States Pharmacopoeia, Volume XXIII (1995), and supplements thereto, under "Chapter <661>, Chemical Resistance-Glass Containers" make excellent storage containers for the physiologically-balanced, electrolyzed, acidic solutions of the present invention. These bottles also meet the requirements for light protection established by the USP under Chapter <661>, "Light Transmission", which may be helpful in some instances. The bottle cap is fabricated from phenolic, and has a liner facing made out of TEFLON® (PTFE) which is less reactive than phenolic, and which helps seal the cap, preventing the passage of ambient air into the bottle. This bottle is available from AllPak Corp., Bridgeville, Pa.

A white (clear) glass bottle produced by the same manufacturer (AllPak Corp.), but absent the amber coloring also appears to function well.

We conducted a study of the shelf life of the solution described above with reference to Tables 2 and 3, in terms of pH and oxidation-reduction potential (ORP) in bottles made out of various materials. Freshly prepared solution was stored over a period of 3 months in 4 types of bottle: The amber glass; the white (clear) glass; High Density PolyEthylene (HDPE); and TEFLON®.

Figure 4A:
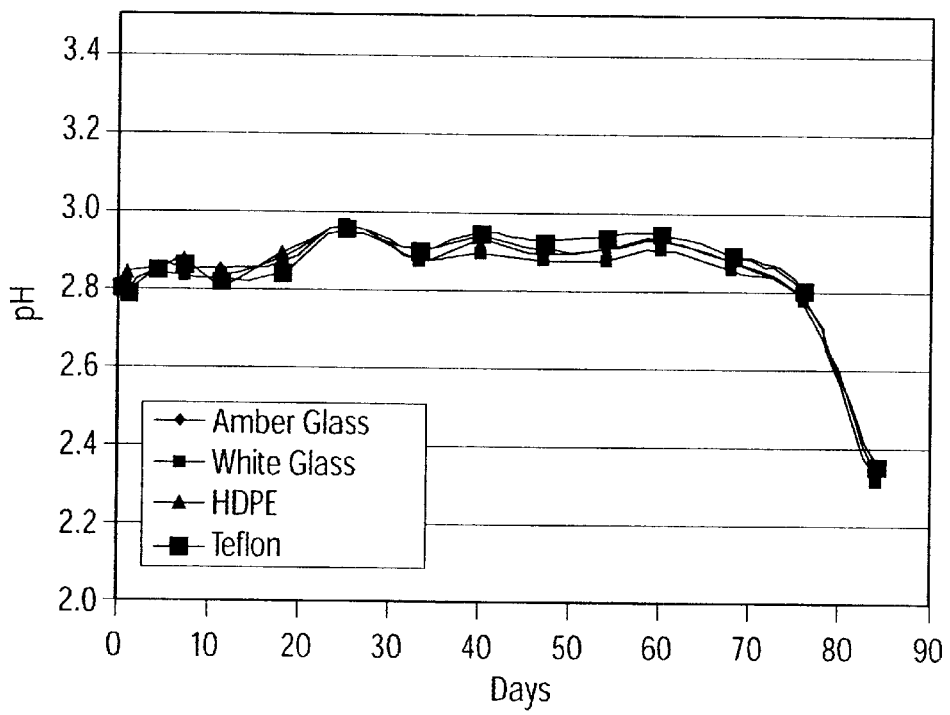
FIG. 4A shows the effect of storage on the pH of the solution.
Figure 4B:
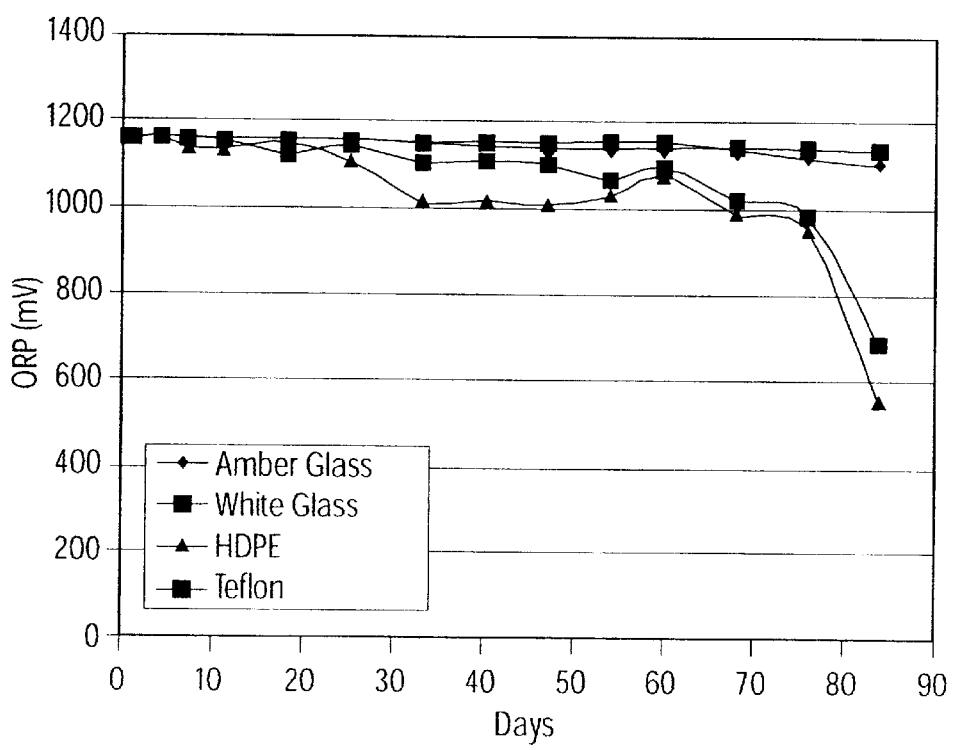
FIG. 4B shows the effect of storage on the ORP of the solution.

At given times, known aliquots were withdrawn to measure the pH and ORP. FIGS. 4A and 4B show the results of known aliquots withdrawn at given times to measure the pH and ORP.

When the physiologically-balanced, electrolyzed, acidic solution of the invention is stored in a glass bottle, the composition has been shown to be stable for at least 60 days. This compares with electrolyzed solutions of sodium chloride described in the prior art, where storage in plastic bottles is recommended, and reported stability is 96 hours or less.

As previously described, electrolysis ionizes the various salts contained in the starting solutions used to generate the physiologically-balanced acidic solutions of the invention to produce oxidizing agents which are known to be involved in physiological systems associated with wound healing and tissue repair and regeneration. Antimicrobial properties of acidic saline solutions prepared solely from sodium chloride salt have been tested against many organisms, as described below.

Antimicrobial Activity

Antimicrobial efficacy of electrolyzed acidic water was tested against microorganisms including *Pseudomonas aeruginosa, Escherichia coli, Staphylococcus aureus, Listeria monocytogenes* 10403s wild type, catalase-deficient mutant *L. monocytogenes* LM1370, *Aspergillus niger* (spores), *Penecillium oblatum* (spores), Lactobacillus, and *E. coli* 0157:H7. Up to 5 logs of reduction in the activity of the microorganisms was achieved after 10 to 60 seconds of exposure to electrolyzed acidic water.

Effects of electrolyzed acidic water on the prevention of hospital-acquired infections (Y. Nakamura and A. Iwasawa, presented at the Japanese Functional Water Symposium, December 1997). Antimicrobial activity of electrolyzed acidic water was tested against 238 strains of 69 species, including bacteria, fungi, and viruses. Three to five logs of reduction in microbial activity were achieved after 5 to 15 seconds of exposure to the electrolyzed acidic water in most cases. Microorganisms used for testing included *S. aureus* (MRSA), *Streptococcus pyogenes, S. pneumoniae, P. aeruginosa, E. coli, E. coli* 0157:H7, *Bacillus cereus, Mycobacterium tuberculosis, Candida albicans, Cryptococcus neoformans, Microsporum canis,* Herpes simplex virus, Influenza virus A/PR/8, and Coxsackie virus A 16, among others.

Eye and Skin Irritation

Primary eye irritation and 5-day skin cumulative irritation studies of electrolyzed acidic water were carried out using male New Zealand white rabbits (M. Takeyoshi et al., presented at the Japanese Functional Water Symposium, 1994). In the primary eye irritation study, 0.1 mL of electrolyzed acidic water was instilled into each eye of six rabbits. In three of the rabbits, the treated eyes were irrigated for 30 seconds after instillation to evaluate the irritation effects. Since no signs of irritation were observed in any of the treated eyes, the electrolyzed acidic water was classified as non-irritating to the rabbit eye according to the AFNOR scale (1992).

In cumulative skin irritation studies, two intact and two abraded skin sites were prepared on the skin on the back of each of six animals. Then, 0.5 mL of electrolyzed acidic water was applied to one intact skin site and one abraded skin site on each animal for 4 hours a day for a period of 5 days; 0.5 mL of distilled water was applied to the second intact skin site and the second abraded skin site on each animal for the same time period, as a control. No cumulative skin irritation effects were noted at the application sites of the electrolyzed acidic water compared to the distilled water.

We have studied the antimicrobial properties of the solutions of the present invention as well as the behavior of these solutions with respect to eye and skin irritation and find exciting results, which are described below.

III. METHODS FOR USING THE COMPOSITION OF THE INVENTION

Application of the physiologically-balanced, electrolyzed, acidic solution of the present invention, which is rich in oxygen and contains some ozone (the key elements in enhancing wound healing), helps wound healing progress remarkably. Antimicrobial properties of acidic electrolyzed salt solutions are such that they enhance the healing process of any wound contaminated with microorganisms. The compositions of the invention function specifically to maintain the necessary antibacterial environment for wounds to heal faster, without the usual complications associated with superficial infections. In addition, the solutions provide topical bacterial control and humidification of chronic wounds. The use of acidic electrolyzed salt solutions has been instrumental in healing a number of patients with deep wounds which were not responding to usual medications and locally applied treatments.

The physiologically balanced, electrolyzed acidic salt solutions of the invention have been shown to be effective at healing wounds that are provided with a good blood supply. Our preliminary studies have indicated that a much faster rate of healing is achieved than with prior art compositions, with patients reporting less pain during their recovery period.

Three recent case studies involving the treatment of human subjects with a preferred composition of the invention are presented below. In these case studies, the electrolyzed acidic salt solution was essentially the same as that described for the Electrolyzed Acidic Solution in Table III. This composition provides osmolarity similar to that of blood plasma. The wounds were kept continuously moist with the composition of the invention, and were covered with Vaseline gauze to prevent evaporation of the solution.

Case Stud #1

The patient was a 70 year-old female, with a long history of severe venous edema, lymphaedema, and obesity. Her vascular supply was normal. She developed a cutaneous ulcer 2 years ago in the lower right leg. A second ulcer subsequently developed in the lateral right leg. The ulcers had previously been treated using multiple methods, including debridement, antibiotics, topical solutions including BETADINE® (Purdue Frederick, Norwalk, Conn.); SILVADINE® (BASF Corporation, Mt. Olive, N.J.); ELASE® (Fujisawa Co., Deerfield, Ill.); and FURACIN® (Roberts Pharmaceutical Corp., Meridian Center, Ill.). By way of explanation, BETADINE® is an antiseptic cleanser, used externally on wounds; an iodine-containing preparation used as a broad spectrum antimicrobial. SILVADINE® is a soft white cream containing 1% silver sulfadiazine antimicrobial agent which is applied to wounds after cleaning and debriding. ELASE® is an enzymatic powder or cream used as a debridement agent in wounds where circulation is poor, to destroy dead tissue and leave healthy tissue intact. FURACIN® is a nitrofurazone broad-spectrum antibacterial cream used against pathogens commonly causing surface infections. Use of these agents in the wound healing had not produced the desired results.

A biopsy revealed benign ulceration and granulation tissue. The possibility of *Pyodermo Gangrenosum* was considered. The initial measurements of these severely necrotic ulcers were 130×180 mm and 98×125 mm. Treatment included bedrest, debridement, antibiotics, and topical application of the composition of the invention, for hydration and topical bacterial control. Within 10 days, the ulcers were almost completely covered with crisp red granulation tissue and the pain was gone. Within 14 days, a split thickness skin graft closed the wound; the patient was able to leave the hospital 8 days later. Within two months following the start of treatment, the ulcers had completely healed, and the patient remained pain-free.

Case Study #2

The patient was a 50 year-old male, with a history of thrombophlebitis, pulmonary emboli, and obesity. The patient had experienced infected hematomatous ulceration in both groins and bilateral venous ulcers in both legs for several months. He had an antithrombin III deficiency and had been coumadinized. By way of explanation, Antithrombin III is a protein consisting of normal plasma and extracellular sites that inactivates thrombin in a time-dependent irreversible reaction and serves as a cofactor of heparin into its anticoagulant activities. Antithrombin III also inhibits certain coagulation factors-occurs in certain disease process i.e. liver disease or may be genetic. Coumadinized refers to the use of crystalline warfarin tabs or Heparin I.V. Anticoagulant to treat patients who have thrombosis to prevent further thrombus. COUMADINE® is manufactured by DuPont® Pharmaceutical, Wilmington, Del.

Because of the recent hemorrhages in his groin, he developed large deep ulcerations on the right (measuring 140×90 mm) and more superficial ulcerations on the left (50×50 mm and 60×60 mm). After the first debridement of infected necrotic fat, the culture revealed the presence of vancomycin-resistant Enterococcus. Treatment consisting of topical application of the composition of the invention was started. Infectious disease consultation recommended no further antibiotic treatment. Topical dressings consisting of sponges soaked with the composition of the invention were packed into the wound and the patient was subjected to bedrest. The distal venous ulcers healed fairly rapidly and required only two more debridements. The left groin ulcer undermined and required opening further while the packing was soaked with the composition of the invention. The patient then began healing, with good granulation tissue forming and epidermal coverage to 90% in the right groin ulcer. The left groin ulcer required debridement for undermining, but began healing without antibiotic treatment.

Case Study #3

The patient was a 57 year-old male, who had experienced recurrent ulcers of both feet and ankles over the past four years. Local wound care had initially been started by coagulating veins and using topical wound therapy. His UNNA® boots caused an increase in his ulcerations, which then became more severe. By way of explanation, an UNNA® boot is an elastic adhesive bandage applied over zinc oxide cream as a protective treatment. An UNNA® boot is a boot-like dressing of the lower extremity made of layers of gauze and UNNA®'s paste; 100% soft cotton gauze impregnated with non-hardening zinc oxide paste. The manufacturer of UNNA®'s paste is Glenwood, Inc. of Tenalty, N.J. He had been using a JOBST® pump for edema control. This pump is designed for intermittent home use and is connected to an inflatable pneumatic appliance which is typically preset to alternate 90 seconds of inflation with 30 seconds of deflation. The manufacturer of JOBST® pumps is Nutech, of San Antonio, Tex.

At the time we examined the patient, his wound measurements were 33×65×2 mm, 17×25×2 mm, and 5×9×2 mm. Physical evaluation verified excellent pulsatile inflow to the leg; the wounds were therefore diagnosed as venous ulcers because of the significant edema present. The patient began compression therapy and debridement, culturing the leg at the same time; the bacteria present were found to be coagulase-negative, methicillin-resistant Staphylococcus and Enterococcus sensitive to vancomycin. He also had Haemophilus and diphtheroids cultured with polymicrobial infection. The patient had persistent nonhealing infections for several months, and the infections had become resistant to the classic antibiotic treatments. The infections were only sensitive to CIPROFLOXACIN® and BACTRIM DS®. CIPROFLOXACIN® is a broad spectrum antibiotic, manufactured by Miles Pharmaceutical, West Haven, Conn., which is active on Gram+ and Gram− bacteria, and is typically used to treat skin, bone and joint infections. BACTRIM DS® is manufactured by Roche of Nutley, N.J. BACTRIM DS® is a sulfonamide antibiotic, which is typically used to treat urinary tract infections, and is also used to treat *E. coli, Proteus species*, Shegellosis and *Pneumocystic pneumonia* infections. The patient was started on CIPROFLOXACIN®, which was then discontinued, and then BACTRIM DS® was started. He had topical debridements.

Since no significant improvement was shown after the treatment described above, topical application of the composition of the invention was begun for control of the bacteria and hydration. The infections were rapidly controlled after the start of treatment with the composition of the invention, and the wounds began healing fairly rapidly. He has now shown healing of the two ulcers, with the final measurements down to 7×41 mm and 7×11 mm on the right medial and lateral ankle, respectively.

Oral Care

The physiologically-balanced, electrolyzed, acidic solution of the invention may be used to treat canker sores (mouth ulcers) or cold sores by rinsing the affected area. The solution can be used by soaking the cold sore 3-4 times a day, each time with 2–3 applications, and putting the solution in contact with the sore for 20–30 seconds. The solution may also be used as a mouth rinse for dental and mouth hygiene and to control infection. In this instance, the solution may be used as a gargling solution to fight throat infection. The solution may be applied with the help of a cotton swab for more specific areas. The solution can be used once or several times a day according to patient's needs and condition.

Ophthalmic Care

The physiologically-balanced, electrolyzed, acidic solution of the invention may be used in place of a saline solution to remove a foreign body from, to rinse, or to irrigate the eyes. It can also be applied topically before or after surgery to disinfect an eye and surrounding tissues. Our studies on rabbits eyes showed that this solution is as safe as saline solution when applied to rabbits' eyes and has no toxicity to the eyes when compared to ophthalmic grade BETADINE® (5%) typically used pre-surgery. The solution can be used once or several times a day according to a patient's needs and condition. The solution can be applied by dropping it directly into the eyes as necessary. It can also be applied by soaking a gauze and applying the saturated gauze to the eyes for 1 or several minutes. It can also be used to clean the eyes by gently wiping the eyes with a saturated gauze. The solution can also be poured into a small eye washer, then the washer is inverted over the eye washer and the eyelid opened and closed several times.

The reader will see that the solution of the invention has applications in the treatment of many different types of wounds, including, without limitation, diabetic ulcers, gangrene, venous ulcers, decubitus ulcers, pressure ulcers, wounds due to bites, acute trauma wounds, surgical wounds and burns. The composition of the invention is also useful as an irrigation solution, for example, during dental, periodontal, and ophthalmic procedures. The composition of the invention can also be used for pre- and post-operative cleaning of tissue sites, and as a gargling solution for treatment of canker sores. In addition, because of its active oxidants, the solution of the invention may be a strong growth factor stimulator in the wound healing process. As such, the solution may find uses in many other applications in which disinfection and growth factor stimulation are desirable.

Method of Wound Care

Patients suffering from long-lasting non-healing wounds should be treated with the physiologically-balanced, electrolyzed, acidic solution of the present invention on a daily basis, typically about 3 times a day. The solution of the invention should used be in place of a saline solution, to control infection and to help the wound healing mechanisms. The solution of the invention may be used as follows: a gauze material or gauze pad is presoaked with enough solution to saturate it and is then squeezed to remove excess solution. This removes species present in the gauze which would react with and reduce the effectivity of the solution of the invention. The gauze is wet after this procedure, but not soaked. Additional solution is then applied to completely wet the gauze, which is then immediately applied to the wound. In the alternative, the gauze may be applied to the wound and then additional solution applied. Typically the wound site is packed with the solution-soaked gauze, and optionally, a vasoline gauze can be applied on top of the packed wound to keep it moist and free of contaminating germs. The wound site is then wrapped with wound dressings as is standard in the art. The solution may also be used to clean a wound by pouring it directly on the wound site to remove any necrotic tissue by a mechanical procedure, and also as a cleanser or irrigant.

The patient may also make use of a "wound care kit" provided by California Pacific Lab which permits the patient to periodically pour the solution of the present invention onto the wound site without having to remove the dressing. This kit provides ease-of-use, portability and dramatically reduce exposure of the wound. The wound care kit includes a package containing the solution of the invention and bandaging material. Preferably the kit contains a package containing the solution of the invention and a specialized bandage for use in combination with the solution. The specialized bandage keeps the skin surrounding the wound dry while the wound is treated. Further, the bandage may be applied in a physician's office or at a hospital, with the patient continuing care at home; may be applied and used at home under the instructions of a physician; or for minor injuries, the wound care kit may be used as an "over the counter" treatment by the patient alone.

IV. DESCRIPTION OF THE WOUND CARE KIT

The wound care kit includes bandaging material and a package of the solution of the invention. Preferably the packaging material provides the kind of non-reactive (with the solution) surface previously described herein. In addition, the bandaging material preferably includes a specially designed wound "bandage" made out of an oxygen-permeable bandage material to prevent the wounded tissue from drying. FIGS. 2A–2C and FIG. 3 describe the bandage and illustrate the use of the bandage on a wound surface, respectively. The bandage is described in more detail subsequently. The kit may also include gauze or a similar material for packing of the wound, to be used in combination with the solution and a bandage.

V. DESCRIPTION OF THE SPECIALIZED BANDAGE

The specialized bandage of the present invention comprises an opening, which may also be described as a "window" through which the solution of the invention or other topical material may be applied periodically as needed depending on the indication. Preferably, the bandage includes a dew/moisture sensor, an electrically-conductive sensor which measures ion content, or other bandage property sensor which provides an indication of the status of the bandage related to treatment of the wound. For example, and not by way of limitation, a dew/moisture indicator which provides a colored indication when the bandage solution content has become low, or a signal-producing device such as a sound indicator or an electrical signal output indicator when the ion content of the treatment solution has become low so that the bandage is no longer sufficiently effective.

Figure 2A:
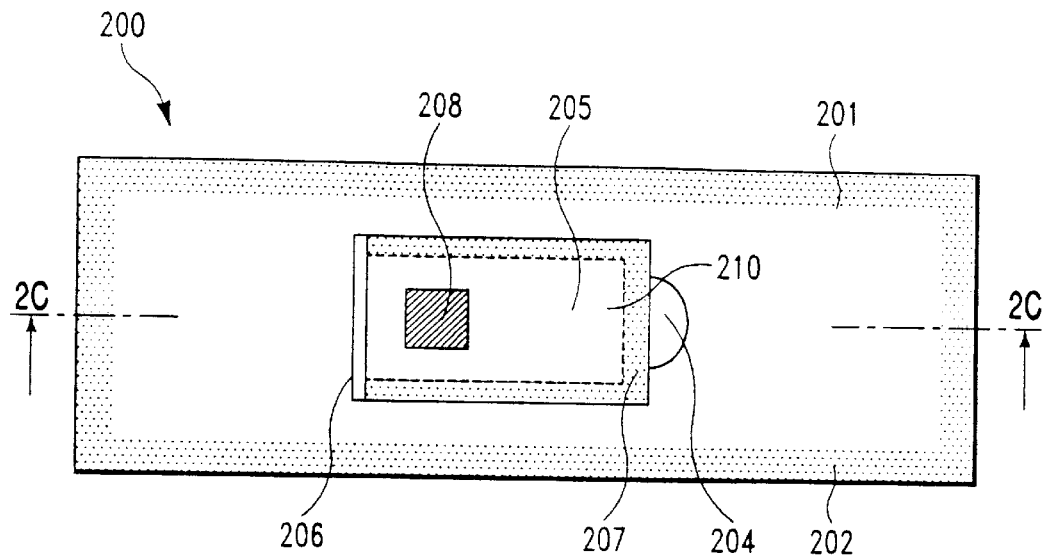
FIG. 2A is a schematic top view of an air-permeable bandage 200, including outer portion 201 having a primary adhesive border 202; an inner portion 210 including a lifting flap 205 having a secondary adhesive border 207, a lifting tab 204, which assists in the lifting of flap 205, a hinge 206, and a dew/humidity indicator 208 (or other sensor/indicator as will be described subsequently herein).
Figure 2B:
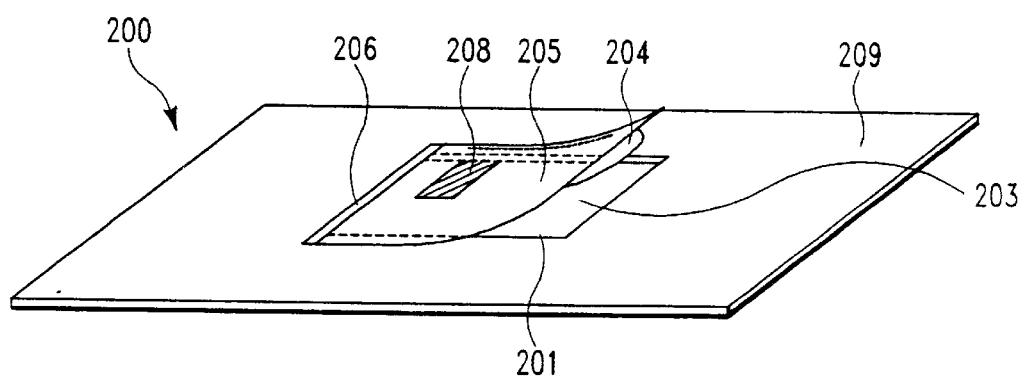
FIG. 2B is a schematic side view of air-permeable bandage 200, showing lifting flap 205 and lifting tab 204 in a partially lifted position, to provide a window opening 203 through bandage 200. A portion of secondary adhesive border 207 has been lifted above the upper surface 209 of bandage 200.
Figure 2C:
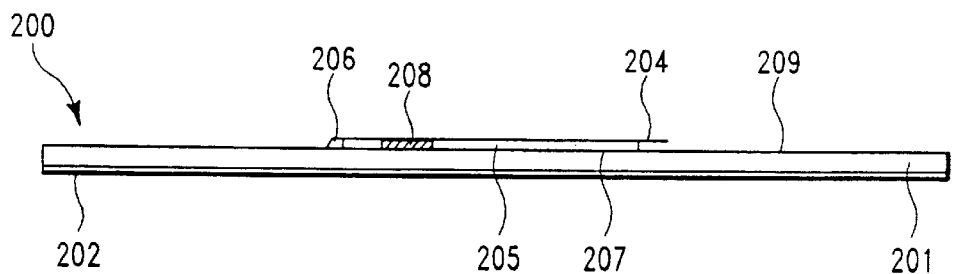
FIG. 2C is a schematic cross-sectional view of air-permeable bandage 200, with lifting flap 205 and lifting tab 204 in a lowered position, secured to upper surface 209 of bandage 200 by secondary adhesive border 207.

One embodiment of the bandage invention is shown in FIGS. 2A–2C, The bandage 200 includes an outer portion 201 having a primary adhesive border 202; an inner portion 210 including a lifting flap 205 having a secondary adhesive border 207, a lifting tab 204, which assists in the lifting of flap 205, and a hinge 206. Optionally the bandage has a dew/humidity indicator 208, or an electrically-conductive sensor, where the sensor may be attached to a signal generator, which occupies a position within inner portion 210 of bandage 200. FIG. 2B is a schematic side view of air-permeable bandage 200, showing lifting flap 205 and lifting tab 204 in a partially lifted position, to provide a window opening 203 through bandage 200. A portion of secondary adhesive border 207 has been lifted above the upper surface 209 of bandage 200. FIG. 2C is a schematic cross-sectional view of air-permeable bandage 200, with lifting flap 205 and lifting tab 204 in a lowered position, secured to upper surface 209 of bandage 200 by secondary adhesive border 207. One skilled in the art can envision a number of similar designs which will accomplish the function and utility of the bandage in a similar manner, and such designs are considered to be included in the present invention.

Figure 3:
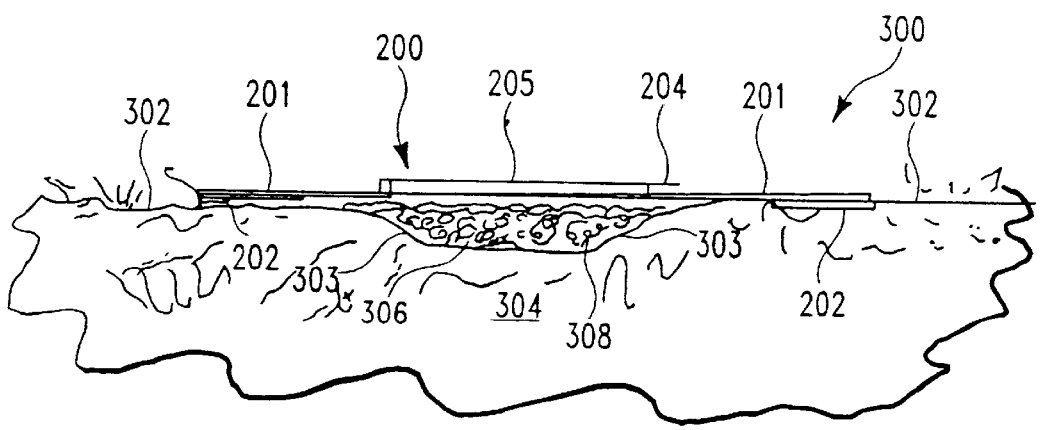
FIG. 3 is a schematic cross-sectional view 300 of an air-permeable bandage 200 of the kind shown in FIGS. 2A–2C, applied over a subcutaneous wound 303. The subcutaneous tissue 304 is packed with gauze 306 which has been soaked in the physiologically balanced, electrolyzed, acidic solution 308 of the present invention. The bandage 200 is adhered to the skin surface 302 by a primary adhesive border 202. Bandage lifting flap 205 can be lifted via tab 204 to expose gauze 306 for the application of additional solution 308 when a dew/humidity indicator (not shown) or other sensing/indication device (not shown) indicates a low level of humidity of the gauze 306.

FIG. 3 is a schematic cross-sectional view 300 of an air-permeable bandage 200 of the kind shown in FIGS. 2A–2C, applied over a subcutaneous wound 303. The subcutaneous tissue 304 is packed with a packing material 306 such as gauze, which has been treated to reduce or eliminate reactivity with oxidants and then soaked in the physiologically balanced, electrolyzed, acidic solution 308 of the present invention. The bandage 200 is adhered to the skin surface 302 by a primary adhesive border 202. Bandage lifting flap 205 can be lifted via tab 204 to expose packing material 306 for the application of additional solution 308 when desired. A dew/humidity indicator (not shown), or electrically-conductive indicator (not shown) may be used to indicate the appropriate time for addition of solution 308.

The bandage provides ease-of-use to the patient by allowing him to pour the solution onto his wound or onto wound packing without having to remove the entire dressing. A more complicated version of the bandage, such as one having an electrically-conductive sensor which may be connected to monitoring equipment is particularly helpful in a hospital setting.

Accordingly, the above described preferred embodiments are not intended to limit the scope of the present invention, as one skilled in the art can, in view of the present disclosure, expand such embodiments to correspond with the subject matter of the invention claimed below.

We claim:

1. A method of promoting wound healing, or tissue repair, or tissue regeneration, in a subject in need of such treatment comprising: applying to a wound, or a damaged tissue, or a combination thereof, with an effective amount of a physiologically-balanced, acidic composition comprising an electrolyzed aqueous solution of halide-comprising salts including about 0.3 to about 14 g/L sodium halide, about 0.02 to about 0.8 g/L potassium halide, and about 0.01–0.5 g/L magnesium halide; and having a total concentration of halide-comprising salts in the range of about 0.4 g/L to about 16 g/L, a pH ranging from about 2 to about 6, an oxidation reduction potential ranging from about +600 mV to about +1200 mV; a titratable halide content ranging from about 20 ppm to about 100 ppm; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

2. A method of treating a burn in a subject in need of such treatment, comprising application of an effective amount of a physiologically-balanced, acidic composition to an affected site of the damaged tissues wherein said composition comprises an electrolyzed aqueous solution of halide-comprising salts including about 0.3 to about 14 g/L sodium halide, about 0.02 to about 0.8 g/L potassium halide, and about 0.01–0.5 g/L magnesium halide; and having a total concentration of halide-comprising salts in the range of about 0.4 g/L to about 16 g/L, a pH ranging from about 2 to about 6, an oxidation reduction potential ranging from about +600 mV to about +1200 mV; a titratable halide content ranging from about 20 ppm to about 100 ppm; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

3. The method of claim 1, wherein said method further, comprising exposing the area of damaged tissue to be irrigated to a physiologically-balanced, acidic composition comprising an electrolyzed aqueous solution of halide-comprising salts including about 0.3 to about 14 g/L sodium halide, about 0.02 to about 0.8 g/L potassium halide, and about 0.01–0.5 g/L magnesium halide; and having a total concentration of halide-comprising salts in the range of about 0.4 g/L to about 16 g/L, a pH ranging from about 2 to about 6, an oxidation reduction potential ranging from about +600 mV to about +1200 mV; a titratable halide content ranging from about 20 ppm to about 100 ppm; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

4. The method of claim 1, wherein said method further comprising applying to a dermal tissue a physiologically-balanced, acidic composition comprising an electrolyzed aqueous solution of halide-comprising salts including about 0.3 to about 14 g/L sodium halide, about 0.02 to about 0.8 g/L potassium halide, and about 0.01–0.5 g/L magnesium halide; and having a total concentration of halide-comprising salts in the range of about 0.4 g/L to about 16 g/L, a pH ranging from about 2 to about 6, an oxidation reduction potential ranging from about +600 mV to about +1200 mV; a titratable halide content ranging from about 20 ppm to about 100 ppm; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

5. The method of claim 1, 2, 3, or 4, wherein the concentration of halide-comprising salts ranges from about 4 g/l to about 12 g/l.

6. The method of claim 5, wherein the halide comprising salts are chloride salts.

7. The method of claim 5, wherein the halide-comprising salts further include at least one salt selected from the group consisting of calcium halide, zinc halide, lithium halide, and beryllium halide.

8. A method of promoting wound healing, or tissue repair, or tissue regeneration in a subject in need of such treatment, comprising: applying to a wound, or a damaged tissue, or a combination thereof with an effective amount of a physiologically-balanced, acidic composition comprising an electrolyzed aqueous solution of salts, including sodium cations at a concentration of about 0.005 to about 7 g/L, potassium cations at a concentration of about 0.005 to about 0.6 g/L, and magnesium cations at a concentration of about 0.005 to about 0.1 g/L; and, a pH ranging from about 2 to about 6, an oxidation reduction potential ranging from about +600 mV to about +1200 mV; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

9. A method of treating a burn in a subject in need of such treatment, comprising application of an effective amount of a physiologically-balanced, acidic composition to an affected area of the damaged tissue, wherein said composition comprises an electrolyzed aqueous solution of salts, including sodium cations at a concentration of about 0.005 to about 7 g/L, potassium cations at a concentration of about 0.005 to about 0.6 g/L, and magnesium cations at a concentration of about 0.005 to about 0.1 g/L; and, a pH ranging from about 2 to about 6, an oxidation reduction potential ranging from about +600 mV to about +1200 mV; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

10. The method of claim 8, wherein said method further comprising exposing the area of damaged tissue to be irrigated to a physiologically-balanced, acidic composition comprising an electrolyzed aqueous solution of salts, including sodium cations at a concentration of about 0.005 to about 7 g/L, potassium cations at a concentration of about 0.005 to about 0.6 g/L, and magnesium cations at a concentration of about 0.005 to about 0.1 g/L; and, a pH ranging from about 2 to about 6, an oxidation reduction potential ranging from about +600 mV to about +1200 mV; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

11. The method of claim 8, wherein said method further comprising applying to said dermal tissue a physiologically-balanced, acidic composition comprising an electrolyzed aqueous solution of salts, including sodium cations at a concentration of about 0.005 to about 7 g/L, potassium cations at a concentration of about 0.005 to about 0.6 g/L, and magnesium cations at a concentration of about 0.005 to about 0.1 g/L; and, a pH ranging from about 2 to about 6, an oxidation reduction potential ranging from about +600 mV to about +1200 mV; an $O_3$ concentration ranging from about 0.001 ppm to about 5 ppm; an $O_2$ concentration ranging from about 5 ppm to about 30 ppm; and, a HClO concentration ranging from about 0.1 ppm to about 1000 ppm.

12. The method of claim 8, 9, 10, or 11, further comprising halide-comprising salts.

13. The method of claim 12, wherein the concentration of halide-comprising salts ranges from about 4 g/l to about 12 g/l.

14. The method of claim 12, wherein the halide comprising salts are chloride salts.

15. The method of claim 12, wherein the halide-comprising salts further include at least one salt selected from the group consisting of calcium halide, zinc halide, lithium halide, and beryllium halide.

* * * * *